United States Patent [19]

Angel et al.

[11] 4,296,373
[45] Oct. 20, 1981

[54] HEMATOLOGY CELL COUNTING APPARATUS INCORPORATING MULTIPLE TRANSDUCERS FOR SEQUENTIAL OPERATION

[75] Inventors: Henry R. Angel, Fairfield; James W. Hennessy, Trumbull, both of Conn.

[73] Assignee: Hycel, Inc., Houston, Tex.

[21] Appl. No.: 57,045

[22] Filed: Jul. 12, 1979

[51] Int. Cl.³ ............................................. G01N 27/00
[52] U.S. Cl. ................................................. 324/71 CP
[58] Field of Search .............. 324/71 CP; 235/92 PC, 235/92 PL; 364/416, 555

[56] References Cited

U.S. PATENT DOCUMENTS 3,921,066  11/1975  Angel ............................. 324/71 CP
4,167,038   9/1979  Hennessy ........................ 324/71 CP Primary Examiner—Michael J. Tokar
Attorney, Agent, or Firm—Tim L. Burgess

[57] ABSTRACT

In particle counting apparatus such as a hematology parameter measurement apparatus for performing multiple measurements on one blood sample, first and second impedance transducers, each including inner and outer electrodes, are provided for selective hydraulic connection to a probe head including one set of pressure ports and a further inner electrode. The first and second transducers are respectively immersed in first and second dilutions of the sample. Measurements on each dilution are made in a conventional manner. The inner electrodes are connected in parallel as are the outer electrodes so that small liquid passageways may be provided between the transducers and the probe head while maintaining a low impedance in the liquid path. Means are provided for selecting the sequence of operations and are provided to increase the throughput of samples for which multiple measurements are made.

9 Claims, 6 Drawing Figures

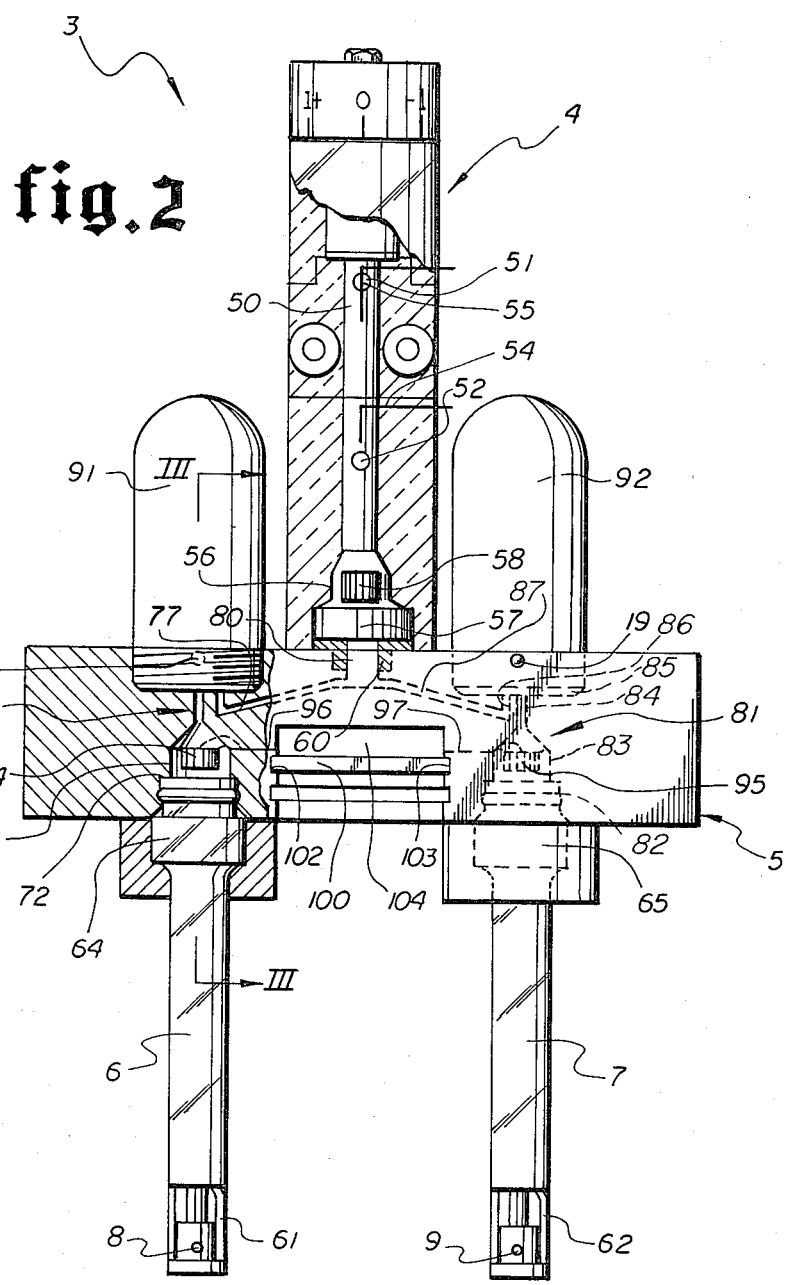

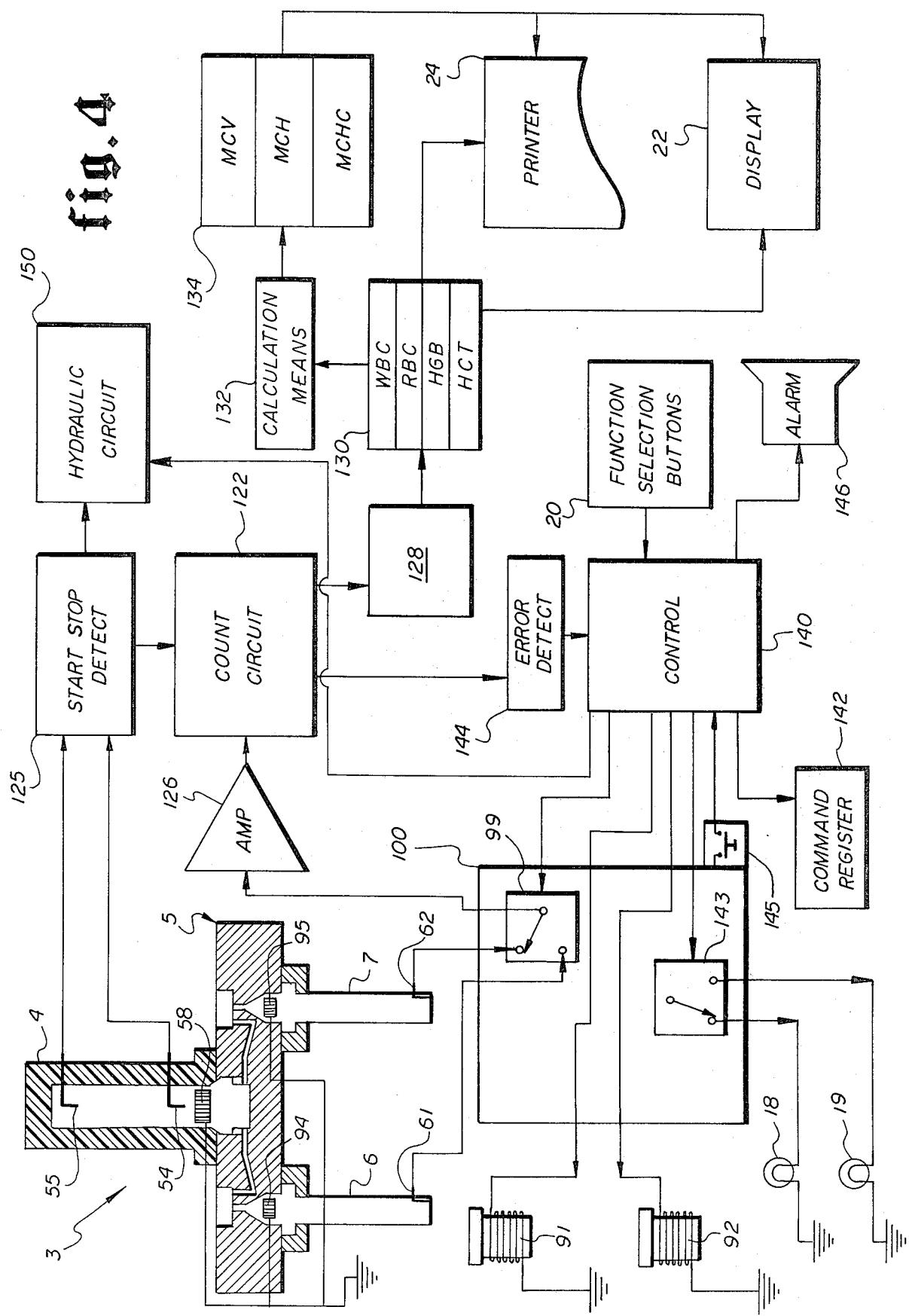

fig.5A

| DEPRESS BUTTON | COMMAND IN REGISTER 142 | OPERATION | SOLENOID 91 | SOLENOID 92 | LAMP 18 LAST USED ON LOW / OTHER OFF | LAMP 19 LAST USED ON LOW / OTHER OFF |
|---|---|---|---|---|---|---|
|  | STAND BY |  | CLOSED | CLOSED |  |  |
| 38 | PUSH RBC/HCT | RBC/HCT | CLOSED | OPEN | OFF | ON-HI |
| 39 | WBC/HGB | WBC/HGB | OPEN | CLOSED | ON-HI | OFF |
| 36 | PRINT | PRINT | CLOSED | CLOSED | ON-LOW | OFF | fig.5B

| DEPRESS BUTTON | COMMAND IN REGISTER 142 | OPERATION | SOLENOID 91 | SOLENOID 92 | LAMP 18 LAST USED ON LOW / OTHER OFF | LAMP 19 LAST USED ON LOW / OTHER OFF |
|---|---|---|---|---|---|---|
|  | STAND BY |  | CLOSED | CLOSED |  |  |
| 38 | RBC/HCT | RBC/HCT (ERROR) | CLOSED | OPEN | OFF | ON-HI |
| 39 | WBC/HGB | WBC/HGB | OPEN | CLOSED | ON-HI | OFF |
|  |  | WAIT | CLOSED | CLOSED | ON-LOW | OFF |
| 36 | PRINT | TOGGEL | CLOSED | OPEN | OFF | ON-LOW |
| SWITCH 145 |  |  |  |  |  |  |
| 34 | -P-R-I-N-T- | BACKFLUSH | CLOSED | OPEN | OFF | ON-HI |
| 38 | RBC/HCT | RBC/HCT | CLOSED | OPEN | OFF | ON-HI |
| 36 | PRINT | PRINT | CLOSED | CLOSED | OFF | ON-LOW |

HEMATOLOGY CELL COUNTING APPARATUS INCORPORATING MULTIPLE TRANSDUCERS FOR SEQUENTIAL OPERATION

BACKGROUND OF THE INVENTION

The present invention relates to particle counters of the impedance measurement type and more specifically to multiple probes in a hematology parameter measurement apparatus.

In the well-known liquid particle counter of the impedance measurement type, discussed here in the context of a hematology parameter measurement apparatus, a transducer may take the form of a conduit having an aperture in one wall and be provided with both an inner electrode within the conduit and an outer electrode. The transducer is immersed in a liquid sample and liquid is aspirated through the aperture into the probe. As particles pass through the aperture, the impedance between the inner and outer electrode increases, producing counting pulses. An example of such an apparatus is disclosed in U.S. Pat. No. 3,921,066 to Henry R. Angel and James W. Hennessey, issued Nov. 18, 1975. This patent is now assigned to the assignee herein, and the disclosure thereof is incorporated herein by reference. In the use of the apparatus disclosed therein and apparatus of other manufacturers intended for the same purpose, one transducer probe is provided for sequential counts of red and white blood cells. In blood cell counting, a blood sample is taken and a first dilution thereof having a ratio on the order of magnitude of 1:250 and a second dilution having a ratio to the original sample on the order of magnitude of 1:62,500 are respectively used for white blood cell counts and red blood cell counts. Lysing reagent is added to the white blood cell count sample to destroy red blood cells. Red blood cell count and white blood cell count dilutions may be measured in pairs for a plurality of patients, or red blood cell count samples and white blood cell count samples may be grouped. Due to the presence of lysing reagent in white blood cell count samples, it is necessary to rinse the transducer probe before running a red blood cell count following a white blood cell count. Thus, the instrument operator has the choice of separating the running of red blood cell counts and white blood cell counts for each patient, or to do both counts for one patient at a time. In the latter situation, a rinse must be performed before each red blood cell count measurement.

While prior art systems have been provided with separate sets of transducers for performing red blood cell counts and white blood cell counts, most notably the Coulter Counter[R] Models, such systems have been, in comparison to other hematology cell counting systems marketed to hematology laboratories, complex and expensive. Other multiple probe systems have been disclosed in the prior art such as in U.S. Pat. No. 3,444,464, issued May 13, 1969 to W. H. Coulter, et al. These systems have not provided for counts performed on a different dillution through each transducer aperture.

SUMMARY OF THE INVENTION

It is therefore a general object of the present invention to provide a liquid particle counting apparatus, particularly a hematology parameter measurement apparatus, incorporating a plurality of transducers each for performing measurements on a separate dilution.

It is a more specific object of the present invention to provide an apparatus of the type described in which a single hydraulic source is selectively connected to each transducer for sequential operation thereof and in which operations are controlled to provide for optimized sample throughput.

It is a further object of the present invention to provide an apparatus of the type described in which hydraulic paths from the transducers to the hydraulic source are made small enough to avoid adverse effects such as bubble formation while providing for impedance levels in the fluid paths which do not interfere with optimal operation.

Briefly stated, in accordance with the present invention, there are provided a plurality of transducer probes, each having inner and outer electrodes and all hydraulically connected to a probe head including a pressure means and a further inner electrode. Means are provided for drawing liquid through each transducer sequentially, whereby one sample count at a time is obtained. All inner electrodes are connected in parallel and outer electrodes are connected in parallel so that hydraulic paths of limited size may be provided without unduly increasing the impedance of each fluid circuit. Control means are provided for selecting the sequence of operations.

BRIEF DESCRIPTION OF THE DRAWINGS

The means by which the foregoing objects and features of invention are achieved are pointed out with particularity in the claims forming the concluding portion of the specification. The invention, both as to its organization and manner of operation may be further understood by reference to the following description taken in connection with the following drawings.

Of the Drawings:

FIG. 2 is a view of the probe and transducer assembly, partially broken away, included in the apparatus of FIG. 1;

FIG. 3 is a partial cross-sectional view taken along line III—III in FIG. 2;

FIG. 4 is a diagram of the apparatus of FIG. 1, partially in mechanical schematic, partially in electrical schematic and partially in blocked diagramatic form; and FIGS. 5A and 5B are charts useful in understanding the operation of the apparatus of FIG. 1.

DESCRIPTION OF THE PREFERRED EMBODIMENT

Figure 1:
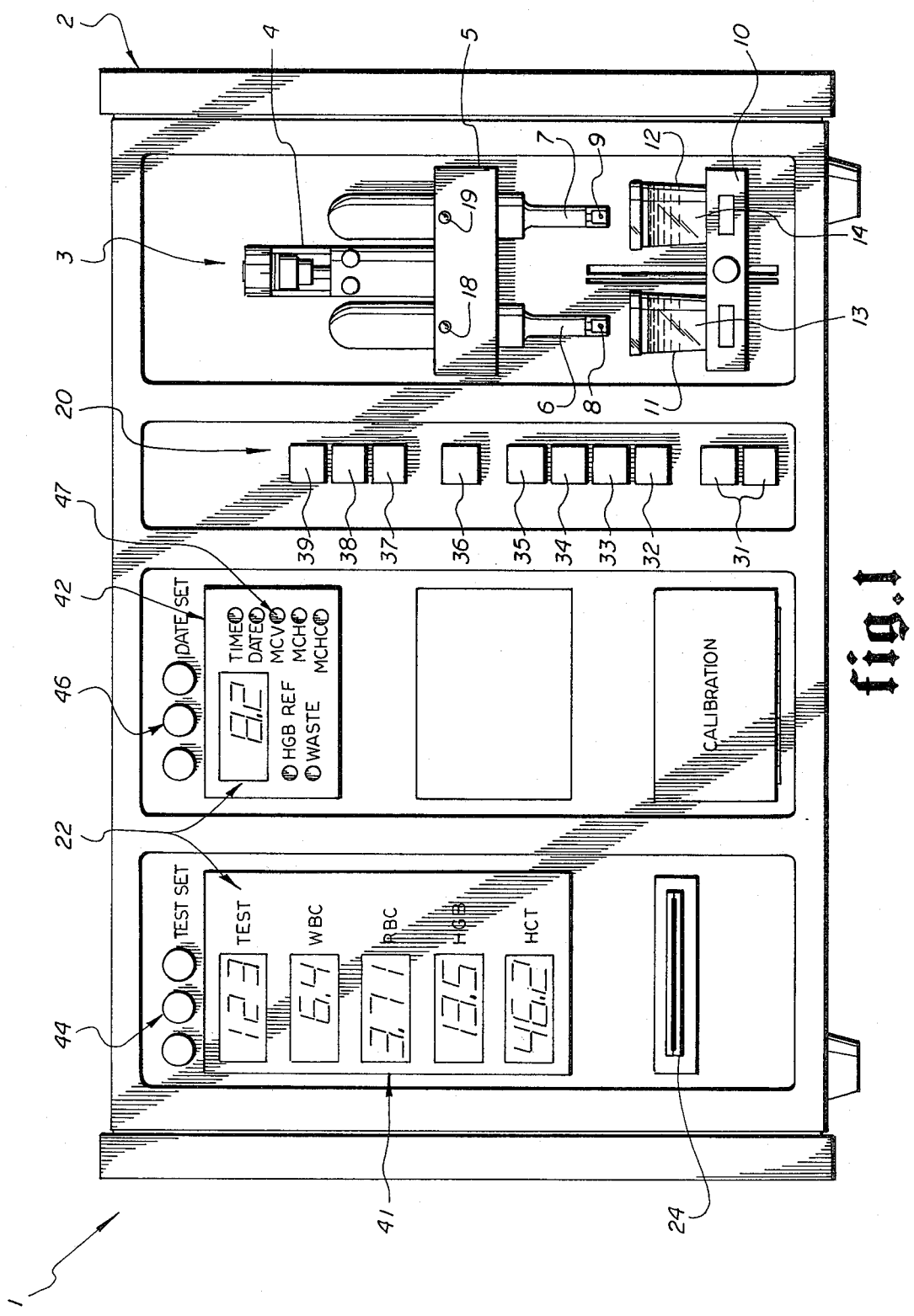
FIG. 1 is an elevation of a hematology parameter measurement apparatus constructed in accordance with the present invention.

FIG. 1 is an elevation of a hematology parameter measurement apparatus 1 constructed in accordance with the present invention. The apparatus 1 includes a housing 2 having mounted thereto a transducer probe assembly 3 including a probe head 4 hydraulically connected to first and second probes 6 and 7. The probes 6 and 7 each respectively include an aperture 8 and 9. In accordance with the present invention, throughput of samples from which multiple dilutions are made and individually measured is increased in an apparatus including a single probe head 4. It is for this reason that two probes 6 and 7 are provided rather than a single transducer as in the patents whose disclosures are incorporated herein by reference. Further in accordance with the present invention, this hydraulic connection is made by a manifold 5 further described below. The apparatus here is similar to that of U.S. patent Ser. No. 842,508 now allowed and issued (U.S. Pat. No. 4,167,038) to James W. Hennessy. This patent is commonly assigned to the assignee herein and the disclosure thereof is incorporated herein by reference. Also incorporated by reference herein, are the disclosures of commonly assigned U.S. Pat., Nos. 4,063,309 to James W. Hennessy and Bruce W. Turner, issued Dec. 13, 1977, entitled "MEAN Corpuscular Volume Measuring Apparatus and Method" and 4,068,169 to Henry R. Angel and Bernard O. Bachenheimer, issued Jan. 10, 1978, and entitled "Method and Apparatus for Determining Hematocrit." The hematology parameter measurement apparatus 1 preferably comprises means for measuring red blood cell count, white blood cell count, hemoglobin, hematocrit, means corpuscular volume, mean corpuscular hematocrit, and mean corpuscular hemoglobin concentration. Details of each measurement are described in the above-cited patents. The present disclosure is primarily directed toward the transducer probe assembly 3 and its interaction in the system of the apparatus 1.

Prior to a more detailed description of the present invention, functions of the apparatus as seen in FIG. 1 are briefly reviewed. A carriage 10 movable between upper and lower positions is provided for supporting at least one sample cup, and in the present embodiment for supporting first and second sample cups 11 and 12. Sample cups 11 and 12 respectively contain samples 13 and 14 which may respectively comprise first and second dilutions of one blood sample. The first dilution 13 may be a dilution on the order of magnitude of 1:250 with lysing reagent added thereto for performance of white blood cell counts. The second dilution 14 may comprise a dilution on the order of magnitude of 1:62,500 for red blood cell counts. After the dilutions 13 and 14 have been prepared by an instrument operator, the sample cups 11 and 12 are placed on the carriage 10 which is moved vertically so that the probes 6 and 7 are immersed in the samples 13 and 14 respectively. Display lamps 18 and 19 are provided, preferably in the manifold 5, to indicate which of the probes 6 or 7 is connected for sample measurement. The lamps 18 and 19, which may also be light emitting diodes are alternately energized. Control circuitry, further described below, synchronizes necessary operations in response to functions selected by an operator achieved through depression of one of a plurality of function selection buttons 20. Results obtained may be viewed on a display means 22 and may also be printed on a print card by a printer 24. The portion of the printer 24 visible in FIG. 1 is a print card input-output slot.

The function selection buttons 20 include a plurality of buttons which may be conveniently interfaced with control circuitry in many different ways in many different embodiments. In the present embodiment, selection buttons 31 through 39 are provided. The selection buttons 31–35 are respectively utilized for the functions of on-off, initiation of a cleaning mode, selection of a calibrating mode, selection of a "backflush" mode for expelling liquid from the transducers 6 and 7 and for reset. Button 36 is utilized to command a print mode when a print card is inserted into the printer 24. Button 37 is used to command a rinse mode in which cleaning liquid may be drawn into the transducer probe assembly 3. Button 38 is used to command a dual mode in which both a white blood cell count and hemoglobin measurements are made and measured values thereof generated. Button 39 is used to command a red blood cell count and hematocrit measurement. In the present embodiment, the display 22 comprises two display portions 41 and 42. The display 41 includes separate display means for providing numerical indications of the arbitrary number assigned to a test sample and what may be referred to as "measured values," i.e., WBC, RBC, HGB, and HCT. A plurality of buttons 44 may be provided which are connected to set the test number and initial sample, and automatic indexing of the test numbers may be provided thereafter. The display portion 42 includes a display area for displaying a calculated value, time of day or date. A plurality of buttons 46 may be provided which are connected to set a date. By depression of button 36 in the absence of a print card in the printer 24 an operator may set the display portion 42 to display different ones of these indications, with the indication being displayed being pointed out by one of a plurality of indicator lights 47 being lighted next to indicia which denote the quantity being displayed.

A detailed description of the invention begins with respect to FIGS. 2 and 3. FIGS. 2 and 3, respectively, are an elevation, partially broken away, of the transducer probe assembly 3 of FIG. 1 and a partial vertical cross-sectional view taken along line III—III at approximately 45° from the plane defined by FIG. 1. The same reference numerals are used to denote elements corresponding to those in FIG. 1. In FIG. 2 the transducer probe assembly 3 includes a volumetric metering chamber comprising a vertically disposed bore 50 within the probe head 4. The bore 50 has a closed upper end and an open lower end for hydraulic connection to the probes 6 or 7. First and second pressure ports 51 and 52 are provided along the bore 50 for aspiration of sample liquid therein and for draining liquid therefrom respectively in a well-known manner. Start and stop electrodes 54 and 55 are provided having ends displaced from each other within the bore 50 and both intermediate the pressure ports 51 and 52. In operation, fluid is drawn into the port 51, and in a well known manner, a count begins when liquid contacts the start electrode 54 and ends when liquid contacts the stop electrode 55. Liquid is then drained through the port 52. The transducer head 4 comprises further bores 56 and 57 concentric with the bore 50 which are axially displaced therefrom to communicate with the lower, open end thereof. The bore 57 is of a diameter for receiving a probe 6 or 7 or, in the present embodiment, hydraulic connector means 60 to the manifold 5. The bore 56 is intermediate bores 57 and 50 and surrounds an inner electrode 58. The inner electrode 58 is selected to be connected to a common terminal and comprises one terminal of impedance sensing means for producing blood cell counts. The other terminal of the impedance means will selectively comprise outer electrode 61 or 62 each respectively being formed on the outer surface of one of the probes 6 and 7. The probe 6 has an upper portion 64 constructed for fitting in the bore 57 or, in the present embodiment, the manifold 5. Similarly, the probe 7 has an upper portion 65 for fitting into the bore 57 or the manifold 5 and communicating with the bore 50.

In order to provide for selective hydraulic connection of the bores 6 or 7 with the transducer head 4 hydraulically and in a further improved manner in accordance with the present invention as further described below, the manifold 5 is provided. The manifold 5 includes a first hydraulic path 71 including a recess 72 for receiving an end 64 of the probe 6. Formed thereabove is a bore 73 communicating with a narrower bore 74 opening into a chamber 75. Extending downwardly from the chamber 75 is a conduit 76 communicating with an upwardly directed conduit 77 opening into a chamber 80 which is provided for communication with the transducer head 4. Similarly, a bore 82 is provided for receiving the upper portion 65 of the probe 7 communicating with a bore 83 formed thereabove connected to an upwardly extending conduit 84 which opens into a chamber 85. Again, extending downwardly from the chamber 85 is a conduit 86 connected to an upwardly extending conduit 87 having an opposite end opening into the chamber 80. The transition from the upwardly extending conduit 74 or 84 to the downwardly extending conduit 76 or 86 is useful in that it provides an improved means of valving the hydraulic paths 71 or 81. Solenoids 91 and 92 are respectively received in the chambers 75 and 85 and are selectively operable between open and closed positions. The solenoids 91 and 92 are operated so that at one time one of the hydraulic circuits 71 and 81 is closed and the other is opened.

Further, in accordance with the present invention, additional inner electrodes 94 and 95 are positioned in the bores 73 and 83 respectively. Connection means 96 and 97 are provided extending from the bores 73 and 83 to outer surfaces of the manifold 5 preferably for connection to a printed circuit board 100 supported in keyways 102 and 103 along walls of a recess 104 formed in the manifold 5. The solenoids 91 and 92 are also connected to the printed circuit board 100. It is significant that the conduits 74, 77 and 84, 87 are of a small diameter. In the present context size of the diameter of the conduit is determined to be large or small by the size of a bubble that could be formed in the hydraulic circuit 71 or 81 in comparison to the sample volume. Presence of bubbles will significantly affect accuracy of cell counts taken since there are no particles in the fluid bubble as there are in the liquid sample 13 or 14. What is a small diameter will be readily apparent to those skilled in the art. As a specific example, in an embodiment in which the start and stop electrodes 54 and 55 are placed such that a sample size of 0.25 ml. is drawn into the transducer probe head 4, a diameter of the conduit of 0.062 inches is small. Bubbles are also highly undesirable in that with bubble at the face at any of the inner electrodes 58, 94 or 95, electrolysis can take place, producing a gas coating on the electrode. This decreases sensitivity of the impedance circuit formed by inner and outer electrodes.

The impedance of this circuit is also affected by the size of the fluid path. Since conductivity of the impedence circuit in the absence of a particle in the aperture 8 or 9 of the probe 6 or 7 is a function of the size of the diluent path and conductivity of the diluent, making the conduits 76, 77, 86 and 87 small increases the impedance of the path. Increased path impedance, as compared to standard prior art impedance sensors, reduces signal to noise ratio. It is therefore desirable to provide for the hydraulic advantages of a small sized liquid path while eliminating the electrical disadvantages thereof. It is for this reason that the further inner electrodes 94 and 95 are provided. In order to reduce the path impedance, the electrodes 58, 94 and 95 are connected in parallel, and the outer electrodes 61 and 62 are selectively switched into the impedance circuit by a switching circuit 99 on the circuit board 100 (FIG. 4).

This is illustrated in FIG. 4 which is a block diagramatic representation of the apparatus of FIGS. 1-3. The same reference numerals are used to denote corresponding components. The common electrodes 58, 94 and 95 are connected to a common terminal. The outer electrodes 61 and 62 which are energized by a current source are connected to a threshold detector and amplifier 120 providing an output to counting circuitry 122 as further described in the above-cited '038 patent to Hennessy. The start and stop electrodes 54 and 55 are connected to a start and stop detect circuit 125 coupled to the count circuit 122 for enabling and disabling the production of counting pulses in a conventional manner. The count circuit 122 provides outputs to switching means 128 for connecting count results such as white blood cell counts, red blood cell counts, hemoglobin and hematocrit to result registers 130. The result registers 130 also provide outputs to calculation means 132 to provide calculated values such as mean corpuscular volume, mean corpuscular hemoglobin concentration and mean corpuscular hematocrit to calculated result register means 134. The register means 130 and 134 are also selectively connected to the display 22 and printer 24 (FIG. 1) by conventional coupling means (not shown). Operation proceeds under the control of a control circuit 140. The function selection buttons 20 are connected to the control circuit 140 and interfaced thereto in a conventional manner. Specific interconnections are routine in the art and are purely a function of the desired operation as recited below. Examples of specific interconnections for specific functions are disclosed in the above-cited '066 patent to Angel et al. The control means 140 are also connected to the solenoids 91 and 92 and to pressure means 150 which can produce suction or vacuum as disclosed in the above-cited '066 patent to Angel et al. The control circuit 140 includes command register means 142 for storing sequential operation command outputs as provided from the function selection buttons 20.

Commands from the control circuit 140 are coupled to the lamps 18 and 19 by a lamp driver circuit 143 on the printed circuit board 100. Each lamp 18 or 19 is illuminated at a high intensity when the solenoid 91 or 92 to which it corresponds is open, and one lamp 18 or 19 is illuminated at a low intensity when both solenoids 91 and 92 are closed to indicate the last-energized solenoid 91 or 92. A switch 145 is located at the printed circuit board 100 and connected to the control circuit 140 to provide a toggle command when actuated to change which of two lamps 18 or 19 is illuminated. The circuitry is interconnected such that the lamp 18 or 19 indicates which solenoid 91 or 92 is currently enabled, i.e. which solenoid will open in response to a backflush command.

An error detection circuit 144 is connected to the control circuit 140. The error detection circuit 144 may, for example, comprise a "clog alarm" as disclosed in the above-cited '066 patent to Angel et al. The control circuit 140 interconnects the error detection circuit 144 so that when a condition sensed as an error with respect to a measurement on a dilution at a probe 6 or 7 is detected, the print command stored in the register 142 is cleared. Preferably an alarm circuit 146 is provided connected to the control circuit 140 to provide an audible alarm in the event of an error. The above-described error detection system and the multiple transducer connection interact to improve apparatus operation to utilize effectively the capability provided by the multiple probes 6 and 7 as described further below.

A sample operating cycle is described with respect to FIGS. 5A and 5B which are charts illustrating operation. FIGS. 5A and 5B also serve to define interconnections in the control circuit 140. In practice, appropriate dilutions 13 and 14 are prepared in the sample cups 11 and 12 respectively which are placed on the carriage 10 in registration with the transducer 6 and 7 respectively. The carriage 10 is elevated so that the transducer 6 is immersed in the sample 13 and the probe 7 is immersed in the sample 14. The function selection buttons 20 may be pressed in a number of different orders. In the present example, the button 38 is depressed first, the button 39 is depressed second and the button 36 is depressed third. Consequently, commands (i) to perform a red blood cell count and hematocrit measurement, (ii) to perform a white blood cell count and hemoglobin measurement, and (iii) to print results by the printer 24, are stored in the command register 142 of the control circuit 140. The red count is first commanded, therefore, the control circuit 140 provides a signal to the solenoids 91 and 92 to open the fluid circuit 81 (FIG. 3) and close the fluid circuit 71. The hydraulic circuit 150 is energized so fluid is aspirated into the pressure port 51. Consequently, sample liquid is drawn from the sample cup 12 through the aperture 9 into the probe 7 through the hydraulic circuit 81 and into the volumetric measuring chamber 50. The liquid level continues rising to the pressure port 51. A red blood cell count begins when the liquid level reaches the start electrode 54 and ends when the liquid level reaches the stop electrode 55. The stop electrode also provides an output to the hydraulic means 150 to initiate draining of liquid through the port 52 in a well-known manner. The count circuit 122 processes the pulse count to produce a red blood cell count and uses the information of the red blood cell count to produce a hematocrit measurement as in the apparatus of the above-cited patent to Angel and Bachenheimer. This function having beem completed, the control circuit 140 provides an output to the solenoids 91 and 92 to close the fluid path 81 and open the fluid path 71. A similar process of drawing liquid into the probe 6 and up to the volumetric measuring chamber 50 is repeated. White blood cell count and hemoglobin results are produced by the count circuit 120. The calculation means 132 also provides calculated results to the result register 134. With all calculations complete, the results are printed on printing media in the printer 24.

In the event of an error, the error detection circuit 144 provides an input to the control circuit 140 to clear the print command in the register 142. Operation proceeds as described above, but the print operation is not performed. The operator may return to the apparatus, simply command a backflush by depression of the button 34 (FIG. 1), first using the switch 145, if necessary, recommand the test for which an error was detected by depressing button 38 or 39, and recommand printing by depression of button 36. The parameter for which an error was detected will be indicated by a prior art response to the output of the error detection circuit 144, e.g. a flashing display as shown in the above-cited '066 patent to Angel et al. Excess repeated operations due to an error condition are eliminated.

It should be noted that no mixing of samples from red and white blood cell counts takes place below the chamber 80 in the manifold 5 (FIG. 3). Therefore, lysing reagent in white blood cell count dilutions will not affect red blood cell counts since the count is a function of particles passing into the probe 7. In this manner, fast and efficient operation is facilitated and only a single transducer head 4 is required for performing multiple cell counting functions. Also, facility in operation is enhanced due to the capability of storing a sequence of operator-selected functions and the ability of an operator to leave the apparatus unattended once a measurement has begun. Printing of a card in an error condition is prevented, and repeat operations in the event of an error condition are minimized.

What is thus provided in accordance with the present invention is an improved apparatus for performing multiple types of cell counts which is efficient in construction and simplified in operation.

What is claimed is new and desired to be secured by Letters Patent of the United States is:

1. In a particle counting apparatus of the impedance sensing type for counting particles passing in a liquid through an aperture by measuring the impedance between inner and outer electrodes on opposite sides of the aperture in the liquid path, including a transducer probe incorporating said aperture and a volumetric metering chamber for metering a predetermined volume of liquid in connection with counting particles, the improvement comprising a conduit system disposed between said transducer probe and said metering chamber in the fluid path, the cross section of the conduit system being of a dimension such that bubbles which can be formed therein are small with respect to the predetermined volume of liquid to be metered by said volumetric metering chamber, and wherein said inner electrode comprises a first impedance measuring inner electrode on that side of the conduit system proximate said transducer probe and a second impedance measuring inner electrode disposed on that side of the conduit system proximate said volumetric metering chamber, said first and second inner electrodes being connected in parallel.

2. In a particle counting apparatus of the impedance sensing type for counting particles passing through an aperture by measuring the impedance between inner and outer electrodes on opposite sides of the aperture in a liquid path, including a transducer probe incorporating said aperture and a volumetric metering chamber for metering a predetermined volume of liquid in connection with counting particles in a sample, the improvement comprising:

a plurality of transducer probes each incorporating an aperture, a conduit system disposed between said transducer probes and said metering chamber, said conduit system including a plurality of fluid paths equal in number to the transducer probes, each such path having first and second ends, the first end of each such path being fluidly connected to a transducer probe and the second end of each such fluid path being fluidly connected to said metering chamber, the cross section of said fluid paths being of a dimension such that bubbles which can be formed therein are small with respect to the predetermined liquid volume to be metered by the metering chamber, closure means for alternatively opening one of said fluid paths and closing the other of said fluid paths, and a plurality of impedance measuring first inner electrodes equal in number to the said transducer probes, each such first inner electrode being disposed in the conduit system on that side of the conduit system proximate the transducer probes.

3. In an apparatus according to claim 2, the improvement wherein an impedance measuring second inner electrode is disposed in the conduit system on that side of the conduit system proximate the said metering chamber, said second inner electrode being connected in parallel with said first inner electrodes.

4. In an apparatus according to one of claims 2 or 3, the improvement in which the outer electrode associated with a probe is switchable into operation simultaneously with operation of said closure means to open the fluid path connected to said probe.

5. Apparatus according to claim 4 in which each of said fluid paths comprises a chamber having an inlet and an outlet extending downwardly therefrom and wherein said closure means comprises means for covering said inlet and outlet.

6. Apparatus according to claim 5 wherein said closure means comprises a solenoid.

7. Apparatus according to claim 5 comprising control means connected to said closure means and function selection means connected to said control means, said function selection means being interconnected such that actuation of one of said function selection means initiates opening of a preselected one of said fluid paths and closing of the other of said fluid paths.

8. Apparatus according to claim 5 wherein said control means further comprises means for storing a plurality of commands, each command being produced in response to actuation of a function selection button.

9. Apparatus according to claim 8 further comprising error detection means and means for outputting data, and wherein said means for storing a plurality of commands includes means for storing a command for outputting data, and wherein said control means comprises means for clearing a command for outputting data in response to an output from said error detection means.

* * * * *